US009822326B2

United States Patent
Patil et al.

(10) Patent No.: US 9,822,326 B2
(45) Date of Patent: Nov. 21, 2017

(54) LOW VISCOSITY, LOW VOLATILITY LUBRICATING OIL BASESTOCKS

(71) Applicants: Abhimanyu O. Patil, Westfield, NJ (US); Satish Bodige, Wayne, NJ (US)

(72) Inventors: Abhimanyu O. Patil, Westfield, NJ (US); Satish Bodige, Wayne, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 122 days.

(21) Appl. No.: 14/623,715

(22) Filed: Feb. 17, 2015

(65) Prior Publication Data

US 2015/0275127 A1 Oct. 1, 2015

Related U.S. Application Data

(60) Provisional application No. 61/972,463, filed on Mar. 31, 2014.

(51) Int. Cl.
*C10M 169/04* (2006.01)
*C07C 43/04* (2006.01)
(Continued)

(52) U.S. Cl.
CPC ......... *C10M 169/042* (2013.01); *C07C 43/04* (2013.01); *C07F 7/0849* (2013.01);
(Continued)

(58) Field of Classification Search
CPC ............ C10M 169/042; C10M 105/76; C10M 139/04; C10M 2227/04; C10M 2227/045; C07C 43/04; C07F 7/0849; C07F 7/1836
See application file for complete search history.

(56) References Cited

U.S. PATENT DOCUMENTS 2,604,487 A * 7/1952 Burkhard ............... C08G 77/48
508/205
2,773,605 A * 12/1956 De Jarnett .............. E21B 19/14
198/560
(Continued)

FOREIGN PATENT DOCUMENTS

EP 0092682 A1 11/1983
EP 0613679 A1 9/1994
(Continued)

OTHER PUBLICATIONS

The International Search Report and Written Opinion of PCT/US2015/016253 dated Jan. 13, 2016.
(Continued)

*Primary Examiner* — Cephia D Toomer
(74) *Attorney, Agent, or Firm* — Robert A. Migliorini

(57) ABSTRACT

This disclosure provides low viscosity, low volatility alkylated siloxane compounds and alkylated alkoxy silane compounds. This disclosure also provides processes for producing the alkylated siloxane compounds and alkylated alkoxy silane compounds, and lubricating oil basestocks and lubricating oils containing one or more of the alkylated siloxane compounds or one or more of the alkylated alkoxy silane compounds. This disclosure further provides a method for improving one or more of solubility and dispersancy of polar additives and/or sludge in a lubricating oil by using as the lubricating oil a formulated oil containing one or more of the alkylated siloxane compounds or one or more of the alkylated alkoxy silane compounds.

18 Claims, 4 Drawing Sheets

(51) Int. Cl.
*C07F 7/08* (2006.01)
*C07F 7/18* (2006.01)
*C10M 139/04* (2006.01)
*C10M 105/76* (2006.01)

(52) U.S. Cl.
CPC ......... *C07F 7/1836* (2013.01); *C10M 105/76* (2013.01); *C10M 139/04* (2013.01); *C10M 2227/04* (2013.01); *C10M 2227/045* (2013.01)

(56) References Cited

U.S. PATENT DOCUMENTS

| | | | |
|---|---|---|---|
| 3,036,003 A | 5/1962 | Verdol | |
| 3,098,825 A | 7/1963 | Shiffler | |
| 3,172,892 A | 3/1965 | Le Suer et al. | |
| 3,219,666 A | 11/1965 | Norman et al. | |
| 3,316,177 A | 4/1967 | Dorer, Jr. | |
| 3,573,334 A * | 3/1971 | Wheeler | C08F 8/42 |
| | | | 204/157.64 |
| 3,632,619 A | 1/1972 | Groenhof | |
| 3,756,052 A | 9/1973 | Quaal et al. | |
| 4,216,970 A | 8/1980 | Wang et al. | |
| 4,234,435 A | 11/1980 | Meinhardt et al. | |
| 4,405,469 A | 9/1983 | Hafner et al. | |
| 4,578,497 A | 3/1986 | Onopchenko et al. | |
| 4,827,064 A | 5/1989 | Wu | |
| 4,827,073 A | 5/1989 | Wu | |
| 4,889,647 A | 12/1989 | Rowan et al. | |
| 4,956,122 A | 9/1990 | Watts et al. | |
| 4,978,464 A | 12/1990 | Coyle et al. | |
| 5,705,458 A | 1/1998 | Roby et al. | |
| 5,981,641 A * | 11/1999 | Takahashi | C08K 3/22 |
| | | | 257/E23.107 |
| 6,887,835 B1 | 5/2005 | Migdal et al. | |
| 7,538,075 B2 * | 5/2009 | Yamada | C08K 3/08 |
| | | | 508/208 |
| 8,563,089 B2 * | 10/2013 | Yoo | C08K 9/06 |
| | | | 427/387 |
| 8,796,190 B2 * | 8/2014 | Kato | H01L 23/3737 |
| | | | 508/150 |
| 8,808,446 B2 * | 8/2014 | Konno | G03F 7/0751 |
| | | | 106/287.12 |
| 2007/0244016 A1 | 10/2007 | Buck et al. | |
| 2008/0058231 A1 | 3/2008 | Yamaguchi et al. | |
| 2008/0058232 A1 | 3/2008 | Yamaguchi et al. | |
| 2011/0239971 A1 | 10/2011 | Nelson et al. | |

FOREIGN PATENT DOCUMENTS

| | | |
|---|---|---|
| EP | 1040115 B1 | 6/2004 |
| EP | 1803798 A2 | 7/2007 |
| GB | 867167 A | 5/1961 |
| GB | 1012324 A | 12/1965 |
| JP | 08337788 | * 12/1996 |
| WO | 99/31113 A1 | 6/1999 |

OTHER PUBLICATIONS

Huang, Junchao et al., Platinum Nano particles from the Hydrosilylation Reaction: Capping Agents, Physical Characterizations, and Electrochemical Properties.

Saxena, Kanak et al., "Synthesis and characterization of some novel silicon esters and their application as lubricant base stock solution," Applied Organometallic Chemistry, 2009, vol. 23, No. 12, pp. 535-540.

* cited by examiner

LOW VISCOSITY, LOW VOLATILITY LUBRICATING OIL BASESTOCKS

CROSS-REFERENCE TO RELATED APPLICATIONS

This application claims priority to U.S. Provisional Application Ser. No. 61/972,463 filed Mar. 31, 2014, which is herein incorporated by reference in its entirety.

FIELD

This disclosure relates to low viscosity, low volatility alkylated siloxane compounds or alkylated alkoxy silane compounds, processes for producing the alkylated siloxane compounds or alkylated alkoxy silane compounds, lubricating oil basestocks and lubricating oils containing one or more of the alkylated siloxane compounds or one or more of the alkylated alkoxy silane compounds, and a method for improving one or more of solubility and dispersancy of polar additives and/or sludge in a lubricating oil by using as the lubricating oil a formulated oil containing one or more of the alkylated siloxane compounds or one or more of the alkylated alkoxy silane compounds.

BACKGROUND

Lubricants in commercial use today are prepared from a variety of natural and synthetic basestocks admixed with various additive packages and solvents depending upon their intended application. The basestocks typically include mineral oils, polyalphaolefins (PAO), gas-to-liquid base oils (GTL), silicone oils, phosphate esters, diesters, polyol esters, and the like.

A major trend for passenger car engine oils (PCEOs) is an overall improvement in quality as higher quality basestocks become more readily available. Typically the highest quality PCEO products are formulated with basestocks such as PAOs or GTL stocks.

PAOs and GTL stocks are an important class of lube basestocks with many excellent lubricating properties, including high viscosity index (VI) but have low polarity. This low polarity leads to low solubility and dispersancy for polar additives and/or sludge generated during service. These basestocks require the use of cobasestocks to improve additive and deposit solubility.

Therefore, there is a need for polar cobase fluids that provide appropriate solubility and dispersibility for polar additives and/or sludge generated during service of lubricating oils.

The present disclosure also provides many additional advantages, which shall become apparent as described below.

SUMMARY

This disclosure provides polar Group V basestocks containing one or more alkylated siloxane compounds or one or more alkylated alkoxy silane compounds. The alkylated siloxane-containing fluids and alkylated alkoxy silane-containing fluids of this disclosure have surprisingly good lubricant properties. Moreover, the alkylated siloxane-containing fluids and alkylated alkoxy silane-containing fluids of this disclosure have surprisingly lower friction coefficient than PAOs of similar viscosity, thus providing fuel economy advantages. The alkylated siloxane-containing fluids and alkylated alkoxy silane-containing fluids of this disclosure are organic molecules containing hydrocarbon and siloxy or silane segments with precise structure (i.e., not polymers).

This disclosure relates in part to compositions comprising one or more compounds represented by the formula:

$$R_1-Si(R_3)_2-O-Si(R_4)_2-R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300; or to compositions comprising one or more compounds represented by the formula:

$$R_5-Si(OR_6)_3 \quad (2)$$

wherein $R_5$ is the residue of an olefin having from about 4 to about 40 carbon atoms; and each $R_6$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300.

This disclosure also relates in part to compositions comprising one or more compounds represented by the formula:

$$R_1-Si(R_3)_2-O-Si(R_4)_2-R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the composition comprising one or more compounds represented by formula (1) is produced by a process which comprises reacting an alkyl siloxane with an olefin, in the presence of a catalyst, under reaction conditions sufficient to produce the composition; wherein the alkyl siloxane has from about 4 to about 20 carbon atoms; and the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300; or to compositions comprising one or more compounds represented by the formula:

$$R_5-Si(OR_6)_3 \quad (2)$$

wherein $R_5$ is the residue of an olefin having from about 4 to about 40 carbon atoms; and each $R_6$ is the same or different and is an alkyl group having from 1 to about 20 carbon atoms; wherein the composition comprising one or more compounds represented by formula (2) is produced by a process which comprises reacting an alkoxy silane with an olefin, in the presence of a catalyst, under reaction conditions sufficient to produce the composition; wherein the alkoxy silane has from about 3 to about 20 carbon atoms; and the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300.

This disclosure further relates in part to a process for preparing a composition comprising one or more compounds represented by the formula:

$$R_1\text{—}Si(R_3)_2\text{—}O\text{—}Si(R_4)_2\text{—}R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the process comprises reacting an alkyl siloxane with an olefin, in the presence of a catalyst, under reaction conditions sufficient to produce the composition; wherein the alkyl siloxane has from about 4 to about 20 carbon atoms; and the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300; or to a process for preparing a composition comprising one or more compounds represented by the formula:

$$R_5\text{—}Si(OR_6)_3 \quad (2)$$

wherein $R_5$ is the residue of an olefin having from about 4 to about 40 carbon atoms; and each $R_6$ is the same or different and is an alkyl group having from 1 to about 20 carbon atoms; wherein the process comprises reacting an alkoxy silane with an olefin, in the presence of a catalyst, under reaction conditions sufficient to produce the composition; wherein the alkoxy silane has from about 3 to about 20 carbon atoms; and the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300.

This disclosure also relates in part to a lubricating oil basestock comprising one or more compounds represented by the formula:

$$R_1\text{—}Si(R_3)_2\text{—}O\text{—}Si(R_4)_2\text{—}R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil basestock has a viscosity ($Kv_{100}$) from about 2 to about 300 cst at 100° C., and a viscosity index (VI) from about −100 to about 300; or a lubricating oil basestock comprising one or more compounds represented by the formula:

$$R_5\text{—}Si(OR_6)_3 \quad (2)$$

wherein $R_5$ is the residue of an olefin having from about 4 to about 40 carbon atoms; and each $R_6$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil basestock has a viscosity ($Kv_{100}$) from about 2 to about 300 cst at 100° C., and a viscosity index (VI) from about −100 to about 300.

This disclosure further relates in part to a lubricating oil comprising a lubricating oil basestock as a major component, and a lubricating oil cobasestock as a minor component; wherein the lubricating oil cobasestock comprises one or more compounds represented by the formula:

$$R_1\text{—}Si(R_3)_2\text{—}O\text{—}Si(R_4)_2\text{—}R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil cobasestock has a viscosity ($Kv_{100}$) from about 2 to about 300 cst at 100° C., and a viscosity index (VI) from about −100 to about 300; or a lubricating oil comprising a lubricating oil basestock as a major component, and a lubricating oil cobasestock as a minor component; wherein the lubricating oil cobasestock comprises one or more compounds represented by the formula:

$$R_5\text{—}Si(OR_6)_3 \quad (2)$$

wherein $R_5$ is the residue of an olefin having from about 4 to about 40 carbon atoms; and each $R_6$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil cobasestock has a viscosity ($Kv_{100}$) from about 2 to about 300 cst at 100° C., and a viscosity index (VI) from about −100 to about 300.

This disclosure yet further relates in part to a method for improving one or more of solubility and dispersancy of polar additives or sludge in a lubricating oil by using as the lubricating oil a formulated oil comprising a lubricating oil basestock as a major component, and a lubricating oil cobasestock as a minor component; wherein the lubricating oil cobasestock comprises one or more compounds represented by the formula:

$$R_1\text{—}Si(R_3)_2\text{—}O\text{—}Si(R_4)_2\text{—}R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil cobasestock has a viscosity ($Kv_{100}$) from about 2 to about 300 cst at 100° C., and a viscosity index (VI) from about −100 to about 300; or the lubricating oil cobasestock comprises one or more compounds represented by the formula:

$$R_5\text{—}Si(OR_6)_3 \quad (2)$$

wherein $R_1$ is the residue of an olefin having from about 4 to about 40 carbon atoms; and each $R_2$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; and wherein the lubricating oil cobasestock has a viscosity (Kv$_{100}$) from about 2 to about 300 cst at 100° C., and a viscosity index (VI) from about −100 to about 300.

In addition to improved solubility and dispersibility for polar additives and/or sludge generated during service of lubricating oils, improved fuel efficiency can also be attained in an engine lubricated with a lubricating oil by using as the lubricating oil a formulated oil in accordance with this disclosure. The formulated oil comprises a lubricating oil basestock as a major component, and an alkylated siloxane-containing or an alkylated alkoxy silane-containing lubricating oil cobasestock as a minor component. The lubricating oils of this disclosure are particularly advantageous as passenger vehicle engine oil (PVEO) products. Optionally, the formulated oil comprises a lubricating oil basestock as a minor component, and an alkylated siloxane-containing or an alkylated alkoxy silane-containing, lubricating oil cobasestock as a major component.

Further objects, features and advantages of the present disclosure will be understood by reference to the following drawings and detailed description.

DETAILED DESCRIPTION OF THE EMBODIMENTS

Figure 1:
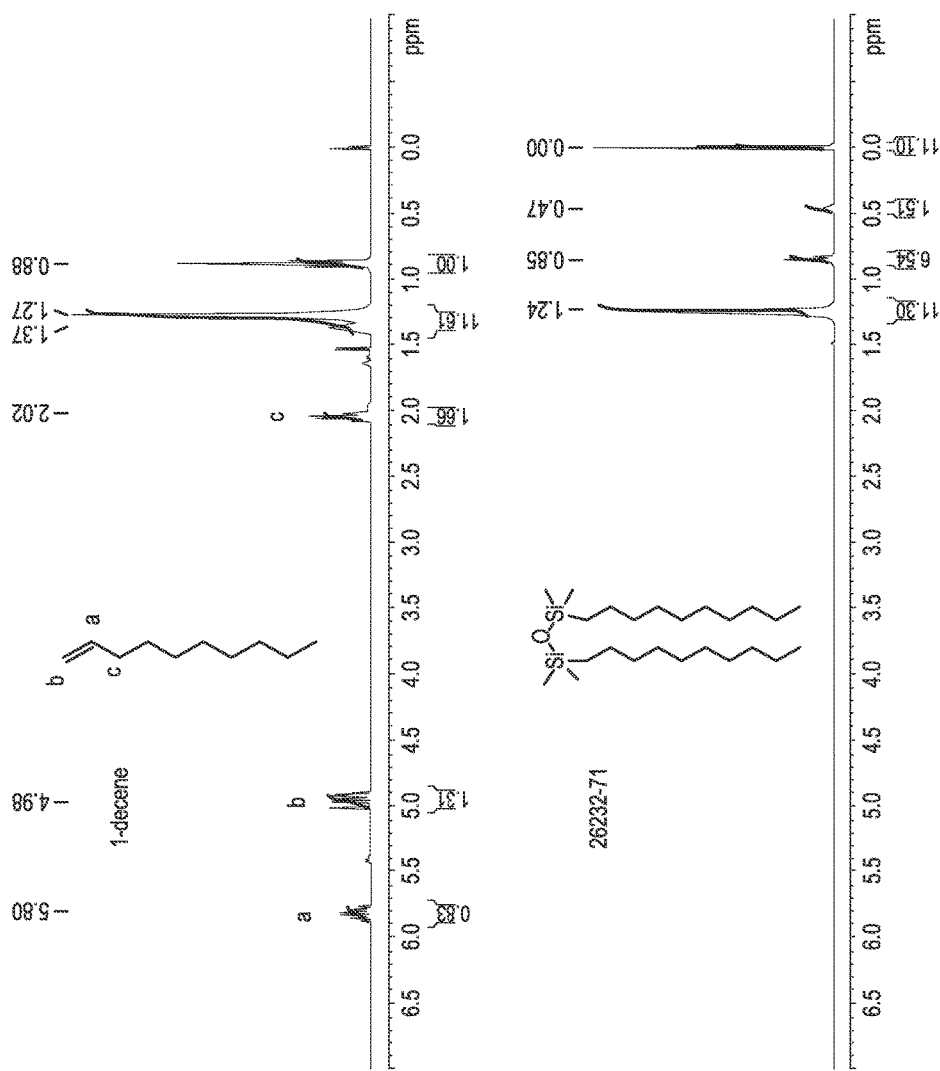
FIG. 1 shows $^1$H NMR spectra for 1-decene starting olefin (top spectrum) and 1,3-didecyl-1,1,3,3-tetramethyl disiloxane (bottom spectrum) for Example 1.

All numerical values within the detailed description and the claims herein are modified by "about" or "approximately" the indicated value, and take into account experimental error and variations that would be expected by a person having ordinary skill in the art.

In an embodiment, this disclosure relates to alkylated siloxane-containing or alkylated alkoxy silane-containing Low Viscosity Low Volatility (LVLV) synthetic basestocks. The products exhibit good lubricant properties.

The compositions of this disclosure possess low viscosity, low Noack volatility and superior low temperature properties. The compositions of this disclosure exhibit excellent bulk flow properties with built-in polarity. The alkylated siloxane-containing fluids and alkylated alkoxy silane-containing fluids of this disclosure are organic molecules containing hydrocarbon and siloxy or silane segments with precise structure (i.e., not polymers).

As indicated above, the fluids of this disclosure comprise one or more compounds represented by formula (1):

$$R_1-Si(R_3)_2-O-Si(R_4)_2-R_2 \qquad (1)$$

wherein R$_1$ and R$_2$ are the same or different and are the residue of an olefin having from about 4 to about 40 carbon atoms; and each R$_3$ and R$_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; or one or more compounds represented by formula (2):

$$R_5-Si(OR_6)_3 \qquad (2)$$

wherein R$_1$ is the residue of an olefin having from about 4 to about 40 carbon atoms; and each R$_2$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin.

The fluids of this disclosure include mixtures. Illustrative mixtures include, for example, two or more compounds represented by formula (1); two or more compounds represented by formula (2); and two or more compounds represented by formula (1) and formula (2).

The fluids of this disclosure have a viscosity (Kv$_{100}$) from about 2 to about 300 cst at 100° C., and a viscosity index (VI) from about −100 to about 300. Preferably, the fluids have a viscosity (Kv$_{100}$) from about 2.1 to about 250 cst at 100° C., more preferably from 2.2 to 200 cst at 100° C., and even more preferably from 2.3 to about 150 cst at 100° C. Preferably, the fluids have a viscosity index (VI) from about −100 to about 300, more preferably from about 0 to 280, and even more preferably from about 50 to 250. As used herein, viscosity (Kv$_{100}$) is determined by ASTM D 445-01, and viscosity index (VI) is determined by ASTM D 2270-93 (1998).

The fluids of this disclosure have a Noack volatility of no greater than 90 percent, preferably no greater than 80 percent, and more preferably no greater than about 50 percent. As used herein, Noack volatility is determined by ASTM D-5800. In particular, the fluids of this disclosure can function in engines without volatilization at specific temperatures (e.g., 247-249° C., Noack conditions).

Illustrative R$_1$, R$_2$ and R$_5$ substituents include, for example, the residue of an aliphatic olefin, an aromatic olefin, a cycloaliphatic olefin, a vinyl ether, an acrylate, a methacrylate, a vinyl ester, a heteroatom-containing olefin, and the like.

Illustrative aliphatic olefins include, for example, alkyl olefins (C$_6$-C$_{40}$) and polyalphaolefin oligomers (C$_6$-C$_{40}$). Illustrative alkyl olefins include, for example, 1-hexene, 1-octene, 1-decene, 1-dodecene, 1-tetradecene, 1-hexadecene, 1-octadecene, and the like. Illustrative polyalphaolefin oligomers include, for example, mPAO dimer (C$_6$-C$_{40}$), trimer (C$_6$-C$_{40}$), tetramer (C$_6$-C$_{40}$), pentamer (C$_6$-C$_{40}$), hexamer (C$_6$-C$_{40}$), and the like.

Illustrative aromatic olefins include, for example, 2,4-dimethylstyrene, 2,5-dimethylstyrene, 4-tert-butylstyrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl]styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, 4-(trifluoromethyl)styrene, and the like.

Illustrative cycloaliphatic olefins include, for example, vinylcyclopentane, vinylcylcohexane, cyclopentene, cyclohexene, cycloheptene, cyclooctene, cyclononene, cyclodecene, cyclododecene, cyclotetradecene, cyclohexadecene, cyclooctadecene, allylcyclohexane, 1,2,4-trivinylcyclohexane, 5-vinyl-2-norbornene, and the like.

Illustrative vinyl ethers include, for example, ethyl vinyl ether, propyl vinyl ether, butyl vinyl ether, isobutyl vinyl ether, 2-ethylhexyl vinyl ether, dodecyl vinyl ether, tetraethylene glycol methyl vinyl ether, hexadecyl vinyl ether, octadecyl vinyl ether, isooctyl vinyl ether, t-butyl vinyl ether, phenyl vinyl ether, cyclohexyl vinyl ether, 2,2,2-trifluoroethyl vinyl ether, 1,4-butanediol divinyl ether, di(ethylene glycol) divinyl ether, tri(ethylene glycol) divinyl ether, 1,4-cyclohexanedimethanol divinyl ether, bis[4-(vinyloxy)butyl]isophthalate, bis[4-(vinyloxy)butyl] succinate, diethyl vinyl orthoformate, di(ethylene glycol) vinyl ether, ethylene glycol vinyl ether, 1,4-butanediol vinyl ether, and the like.

Illustrative acrylates include, for example, methyl acrylate, ethyl acrylate, hexyl acrylate, isooctyl acrylate, isodecyl acrylate, lauryl acrylate, octadecyl acrylate, di(ethylene glycol) 2-ethylhexyl ether acrylate, di(ethylene glycol) ethyl ether acrylate, ethylene glycol phenyl ether acrylate, 2-ethylhexyl acrylate, butyl acrylate, isobornyl acrylate, ethylene glycol methyl ether acrylate, 2-(dimethylamino)ethyl acrylate, 2-(diethylamino)ethyl acrylate, 3-(dimethylamino)propyl acrylate, pentafluorophenyl acrylate, 1,6-hexanediol diacrylate, trimethylolpropane triacrylate, 4-acetoxyphenethyl acrylate, 4-allyloxy-2-hydroxybenzophenone, 2-(4-benzoyl-3-hydroxyphenoxy)ethyl acrylate, 4-acryloylmorpholine, 4-tert-butylcyclohexyl acrylate, tetrahydrofurfutyl acrylate, 3,5,5-trimethylhexyl acrylate, di(trimethylolpropane) tetraacrylate, tris[2-(acryloyloxy)ethyl]isocyanurate, pentaerythritol tetraacrylate, 1,3,5-triallyl-1,3,5-triazine-2,4,6 (1H,3H,5H)-trione, 1,3,5-triacryloylhexahydro-1,3,5-triazine, 1,1,1,3,3,3-hexafluoroisopropyl acrylate, 9H-carbazole-9-ethyl acrylate, 2-hydroxypropyl 2-(methacryloyloxy)ethyl phthalate, and the like.

Illustrative methacrylates include, for example, methyl methacrylate, butyl methacrylate, tert-butyl methacrylate, hexyl methacrylate, 2-ethylhexyl methacrylate, 2-(dimethylamino)ethyl methacrylate, 2-(diethylamino)ethyl methacrylate, di(ethylene glycol) methyl ether methacrylate, lauryl methacrylate, stearyl methacrylate, isobornyl methacrylate, ethylene glycol phenyl ether methacrylate, phenyl methacrylate, cyclohexyl methacrylate, allyl methacrylate, vinyl methacrylate, benzyl methacrylate, 1,6-hexanediol dimethacrylate, bisphenol A dimethacrylate, bisphenol A glycerolate dimethacrylate, 2-[3-(2H-benzotriazol-2-yl)-4-hydroxyphenyl]ethyl methacrylate, cyclohexyl methacrylate, tetrahydrofurfutyl methacrylate, 2-(tert-butylamino)ethyl methacrylate, 2-(diisopropylamino)ethyl methacrylate, 2-N-morpholinoethyl methacrylate, 9H-carbazole-9-ethyl methacrylate, 1-naphthyl methacrylate, pentafluorophenyl methacrylate, 1-pyrenemethayl methacrylate, TEMPO methacrylate, N-(triphenylmethyl) methacrylamide, and the like.

Illustrative vinyl esters include, for example, vinyl acetate, vinyl propionate, vinyl valerate, vinyl butyrate, vinyl decanoate, vinyl stearate, vinyl cinnamate, allyl butyrate, vinyl pivalate, vinyl benzoate, vinyl 4-t-butylbenzoate, allyl cinnamate, and the like.

Illustrative heteroatom-containing olefins include, for example, N-methyl-N-vinylacetamide, N,N-dimethylacrylamide, 4-vinylpyridine, 2-vinylpyridine, 1-vinyl-2-pyrrolidinone, 1-vinyl-1,2,4-triazole, 1-vinylimidazole, N-vinylcaprolactone, 4-acryloylmorpholine, 5-vinyluracil, 4-acryloylmorpholine, N,N-dimethylacrylamide, 2-vinyl-1,3-dioxolane, acrolein diethyl acetal, acrolein dimethyl acetal, 4-vinyl-1,3-dioxolane-2-one, vinylbenzoic acid, 1-vinylbenzyl alcohol, vinyl trifluoroacetate, 1-vinyl cyclohexanole, vinyloxy trimethylsilane, vinyltrimethylsilane, allyl trimethylsilane, triphenyl(vinyl)silane, 2-isopropenyl-2-oxazoline, and the like.

Illustrative $R_3$, $R_4$ and $R_6$ substituents include, for example, linear or branched alkyl groups having from 1 to about 20 carbon atoms, preferably linear or branched alkyl groups having from 1 to 10 carbon atoms, and more preferably linear or branched alkyl groups having from 1 to about 8 carbon atoms. Illustrative $R_3$, $R_4$ and $R_6$ substituents include, for example, methyl, ethyl, propyl, butyl, pentyl, hexyl, heptyl, octyl, and the like.

Illustrative compounds of formula (1) include, for example those represented by the formula:

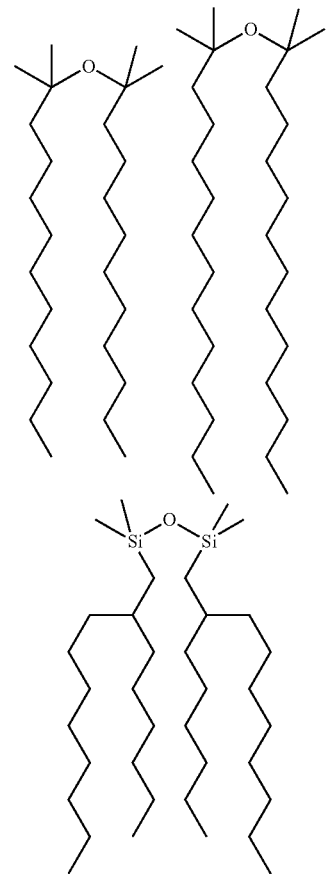

Illustrative compounds of formula (2) include, for example those represented by the formula:

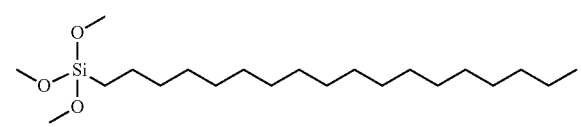 [SMILES: CCCCCCCCCCCCCCCCCC[Si](OC)(OC)OC]

The compositions comprising one or more compounds represented by formula (1) of this disclosure can be prepared by a process that involves reacting an alkyl siloxane with an olefin. The reaction is carried out in the presence of a catalyst. The reaction is also carried out under reaction conditions sufficient to produce a composition comprising one or more compounds represented by formula (1).

Illustrative alkyl siloxanes useful in the process of this disclosure include, for example, 1,1,3,3-tetramethyldisiloxane, 1,1,3,3-tetramethyldisilazane, 1,3-didecyl-1,1,3,3-tetramethyl disiloxane, 1,3-didodecyl-1,1,3,3-tetramethyl disiloxane, 3-di(2-hexyldecyl)-1,1,3,3-tetramethyl disiloxane, 1,3-bis(3-(2-hydroxyethyoxy)propyl)tetramethyldisiloxane, 1,3-bis(hydroxypropyl)tetramethyldisiloxane, bis(methoxytriethyleneoxypropyl)tetramethyldisiloxane, 1,3-bis(trimethylsiloxy)1,3-dimethyldisiloxane, 1,3-bis(heptadecafluoro-1,1,2,2-tetrahydrodecyl) tetramethyldiloxane, 1,3-bis(3-hydroxyisobutyl) tetramethyldisiloxane, 1,3-di-n-butyltetramethyldiloxane, 1,3-diallyltetramethyldisiloxane, and the like.

Illustrative olefins useful in the process of this disclosure include, for example, aliphatic olefins, aromatic olefins, cycloaliphatic olefins, vinyl ethers, acrylates, methacrylates, vinyl esters, heteroatom-containing olefins, and the like. Illustrative of such olefins are described herein.

Preferred olefins include aliphatic olefins, for example, alkyl olefins ($C_6$-$C_{40}$) and polyalphaolefin oligomers ($C_6$-$C_{40}$). Illustrative alkyl olefins include, for example, 1-hexene, 1-octene, 1-decene, 1-dodecene, 1-tetradecene, 1-hexadecene, 1-octadecene, and the like. Illustrative polyalphaolefin oligomers include, for example, mPAO dimer ($C_6$-$C_{40}$), trimer ($C_6$-$C_{40}$), tetramer ($C_6$-$C_{40}$), pentamer ($C_6$-$C_{40}$), hexamer ($C_6$-$C_{40}$), and the like.

Illustrative catalysts that can be used in the process of this disclosure include, for example, metal oxide catalysts such as platinum oxide, and the like. The catalyst can be used in conventional amounts needed to catalyze the reaction of the alkyl siloxane and the olefin.

Other illustrative reaction ingredients include, for example, solvents such as toluene, xylene, decane, hexane, heptanes, and the like.

Reaction conditions for the reaction of the alkyl siloxane and the olefin, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from 1 to 36 hours, and more preferably from about 2 to 24 hours.

The compositions comprising one or more compounds represented by formula (2) of this disclosure can be prepared by a process that involves reacting an alkoxy silane with an olefin. The reaction is carried out in the presence of a catalyst. The reaction is also carried out under reaction conditions sufficient to produce a composition comprising one or more compounds represented by formula (2).

Illustrative alkoxy silanes include, for example, trimethoxysilane, triethoxysilane, tetraphenoxysilane, triethoxy(octyl)silane, dodecyltriethoxysilane, hexadecyltrimethoxysilane, 1H,1H,2H,2H-perfluorooctyltriethoxysilane, 1H,1H,2H,2H-perfluorodecyltriethoxysilane, tetradecamethylhexasiloxane, 11-acetoxyundecyltriethoxysilane, 11-allyloxyundecyltrimethoxysilane, isooctyl trimethoxysilane, triethoxy phenylsilane, (trimethyoxysily) cyclohexane, and the like.

Illustrative olefins useful in the process of this disclosure include, for example, aliphatic olefins, aromatic olefins, cycloaliphatic olefins, vinyl ethers, acrylates, methacrylates, vinyl esters, heteroatom-containing olefins, and the like. Illustrative of such olefins are described herein.

Preferred olefins include aliphatic olefins, for example, alkyl olefins ($C_6$-$C_{40}$) and polyalphaolefin oligomers ($C_6$-$C_{40}$). Illustrative alkyl olefins include, for example, 1-hexene, 1-octene, 1-decene, 1-dodecene, 1-tetradecene, 1-hexadecene, 1-octadecene, and the like. Illustrative polyalphaolefin oligomers include, for example, mPAO dimer ($C_6$-$C_{40}$), trimer ($C_6$-$C_{40}$), tetramer ($C_6$-$C_{40}$), pentamer ($C_6$-$C_{40}$), hexamer ($C_6$-$C_{40}$), and the like.

Illustrative catalysts that can be used in the process of this disclosure include, for example, metal oxide catalysts such as platinum oxide, chloroplatinic acid hydrate $H_2[PtCl_6] \cdot 6H_2O$, and the like. The catalyst can be used in conventional amounts needed to catalyze the reaction of the alkoxy silane and the olefin.

Other illustrative reaction ingredients include, for example, solvents such as toluene, xylene, decane, hexane, heptanes, 2-propanol, and the like.

Reaction conditions for the reaction of the alkoxy silane and the olefin, such as temperature, pressure and contact time, may also vary greatly and any suitable combination of such conditions may be employed herein. The reaction temperature may range between about 25° C. to about 250° C., and preferably between about 30° C. to about 200° C., and more preferably between about 60° C. to 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 48 hours, preferably from 1 to 36 hours, and more preferably from about 2 to 24 hours.

Examples of techniques that can be employed to characterize the compositions formed by the process described above include, but are not limited to, analytical gas chromatography, nuclear magnetic resonance, thermogravimetric analysis (TGA), inductively coupled plasma mass spectrometry, differential scanning calorimetry (DSC), volatility and viscosity measurements.

This disclosure provides lubricating oils useful as engine oils and in other applications characterized by excellent solvency and dispersancy characteristics. The lubricating oils are based on high quality basestocks including a major portion of a hydrocarbon base fluid such as a PAO or GTL with a secondary cobasestock component which is an alkylated siloxane-containing fluids or an alkylated alkoxy silane-containing fluid as described herein. The lubricating oil basestock can be any oil boiling in the lube oil boiling range, typically between 100 to 450° C. In the present specification and claims, the terms base oil(s) and basestock(s) are used interchangeably.

The viscosity-temperature relationship of a lubricating oil is one of the critical criteria which must be considered when selecting a lubricant for a particular application. Viscosity Index (VI) is an empirical, unitless number which indicates the rate of change in the viscosity of an oil within a given temperature range. Fluids exhibiting a relatively large change in viscosity with temperature are said to have a low viscosity index. A low VI oil, for example, will thin out at elevated temperatures faster than a high VI oil. Usually, the high VI oil is more desirable because it has higher viscosity at higher temperature, which translates into better or thicker lubrication film and better protection of the contacting machine elements.

In another aspect, as the oil operating temperature decreases, the viscosity of a high VI oil will not increase as much as the viscosity of a low VI oil. This is advantageous because the excessive high viscosity of the low VI oil will decrease the efficiency of the operating machine Thus high VI (HVI) oil has performance advantages in both high and low temperature operation. VI is determined according to ASTM method D 2270-93 [1998]. VI is related to kinematic viscosities measured at 100° C. using ASTM Method D 445-01.

Lubricating Oil Basestocks

A wide range of lubricating oils is known in the art. Lubricating oils that are useful in the present disclosure are both natural oils and synthetic oils. Natural and synthetic oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve the at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad categories of base oil stocks developed and defined by the American Petroleum Institute (API Publication 1509; www.API.org) to create guidelines for lubricant base oils. Group I basestocks generally have a viscosity index of between about 80 to 120 and contain greater than about 0.03% sulfur and less than about 90% saturates. Group II basestocks generally have a viscosity index of between about 80 to 120, and contain less than or equal to about 0.03% sulfur and greater than or equal to about 90% saturates. Group III stock generally has a viscosity index greater than 120 and contains less than or equal to about 0.03% sulfur and greater than about 90% saturates. Group IV includes polyalphaolefins (PAO). Group V basestocks include basestocks not included in Groups I-IV. The table below summarizes properties of each of these five groups.

| | Base Oil Properties | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | Includes polyalphaolefins (PAO) products | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful in the present disclosure. Natural oils vary also as to the method used for their production and purification, for example, their distillation range and whether they are straight run or cracked, hydrorefined, or solvent extracted.

Group II and/or Group III hydroprocessed or hydrocracked basestocks, as well as synthetic oils such as polyalphaolefins, alkyl aromatics and synthetic esters, i.e. Group IV and Group V oils are also well known basestock oils.

Synthetic oils include hydrocarbon oil such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil basestocks, the Group IV API basestocks, are a commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073, which are incorporated herein by reference in their entirety. Group IV oils, that is, the PAO basestocks have viscosity indices preferably greater than 130, more preferably greater than 135, still more preferably greater than 140.

Esters in a minor amount may be useful in the lubricating oils of this disclosure. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols such as the neopentyl polyols; e.g., neopentyl glycol, trimethylol ethane, 2-methyl-2-propyl-1,3-propanediol, trimethylol propane, pentaerythritol and dipentaerythritol with alkanoic acids containing at least about 4 carbon atoms, preferably $C_5$ to $C_{30}$ acids such as saturated straight chain fatty acids including caprylic acid, capric acids, lauric acid, myristic acid, palmitic acid, stearic acid, arachic acid, and behenic acid, or the corresponding branched chain fatty acids or unsaturated fatty acids such as oleic acid, or mixtures of any of these materials.

Esters should be used in an amount such that the improved wear and corrosion resistance provided by the lubricating oils of this disclosure are not adversely affected.

Non-conventional or unconventional basestocks and/or base oils include one or a mixture of basestock(s) and/or base oil(s) derived from: (1) one or more Gas-to-Liquids (GTL) materials, as well as (2) hydrodewaxed, or hydroisomerized/cat (and/or solvent) dewaxed basestock(s) and/or base oils derived from synthetic wax, natural wax or waxy feeds, mineral and/or non-mineral oil waxy feed stocks such as gas oils, slack waxes (derived from the solvent dewaxing of natural oils, mineral oils or synthetic oils; e.g., Fischer-Tropsch feed stocks), natural waxes, and waxy stocks such as gas oils, waxy fuels hydrocracker bottoms, waxy raffinate, hydrocrackate, thermal crackates, foots oil or other mineral, mineral oil, or even non-petroleum oil derived waxy materials such as waxy materials recovered from coal liquefaction or shale oil, linear or branched hydrocarbyl compounds with carbon number of about 20 or greater, preferably about 30 or greater and mixtures of such basestocks and/or base oils.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL basestocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL basestock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL basestock(s) and/or base oil(s) derived from GTL materials, especially, hydrodewaxed or hydroisomerized/followed by cat and/or solvent dewaxed wax or waxy feed, preferably F-T material derived basestock(s) and/or base oil(s), are characterized typically as having kinematic viscosities at 100° C. of from about 2 mm$^2$/s to about 50 mm$^2$/s (ASTM D445). They are further characterized typically as having pour points of $-5°$ C. to about $-40°$ C. or lower (ASTM D97). They are also characterized typically as having viscosity indices of about 80 to 140 or greater (ASTM D2270).

In addition, the GTL basestock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL basestock(s) and/or base oil(s) typically have very low sulfur and nitrogen content, generally containing less than 10 ppm, and more typically less than about 5 ppm of each of these elements. The sulfur and nitrogen content of GTL basestock(s) and/or base oil(s) obtained from F-T material, especially F-T wax, is essentially nil. In addition, the absence of phosphorous and aromatics make this materially especially suitable for the formulation of low SAP products.

The term GTL basestock and/or base oil and/or wax isomerate basestock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL basestock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, Group V and Group VI oils and mixtures thereof, preferably API Group II, Group III, Group IV, Group V and Group VI oils and mixtures thereof, more preferably the Group III to Group VI base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as received" basis. Even in regard to the Group II stocks, it is preferred that the Group II stock be in the higher quality range associated with that stock, i.e. a Group II stock having a viscosity index in the range 100<VI<120.

In addition, the GTL basestock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL basestock(s) and/or base oil(s) and hydrodewaxed, or hydroisomerized/cat (and/or solvent) dewaxed basestock(s) and/or base oil(s) typically have very low sulfur and nitrogen content, generally containing less than 10 ppm, and more typically less than about 5 ppm of each of these elements. The sulfur and nitrogen content of GTL basestock(s) and/or base oil(s) obtained from F-T material, especially F-T wax, is essentially nil. In addition, the absence of phosphorous and aromatics make this material especially suitable for the formulation of low sulfur, sulfated ash, and phosphorus (low SAP) products.

The basestock component of the present lubricating oils will typically be from 1 to 99 weight percent of the total composition (all proportions and percentages set out in this specification are by weight unless the contrary is stated) and more usually in the range of 10 to 99 weight percent.

Cobasestock Components

Cobasestock components useful in this disclosure include, for example, fluids containing one or more compounds represented by formula (1):

$$R_1\text{—Si}(R_3)_2\text{—O—Si}(R_4)_2\text{—}R_2 \quad (1)$$

wherein $R_1$ and $R_2$ are the same or different and are the residue of an olefin having from about 4 to about 40 carbon atoms; and each $R_3$ and $R_4$ are the same or different and are an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin; or fluids containing one or more compounds represented by formula (2):

$$R_5\text{—Si}(OR_6)_3 \quad (2)$$

wherein $R_1$ is the residue of an olefin having from about 4 to about 40 carbon atoms; and each $R_2$ is the same or different and is an alkyl group having from 1 to about 20 carbon atoms; wherein the olefin is selected from the group consisting of an aliphatic olefin, an aromatic olefin, a cycloaliphatic olefin, a vinyl ether, an acrylate, a methacrylate, a vinyl ester, and a heteroatom-containing olefin.

The fluids of this disclosure include mixtures. Illustrative mixtures include, for example, two or more compounds represented by formula (1); two or more compounds represented by formula (2); and two or more compounds represented by formula (1) and formula (2).

The fluids of this disclosure have a viscosity ($Kv_{100}$) from about 2 to about 300 cst at 100° C., and a viscosity index (VI) from about −100 to about 300. Preferably, the fluids have a viscosity ($Kv_{100}$) from about 2.1 to about 250 cst at 100° C., more preferably from 2.2 to 200 cst at 100° C., and even more preferably from 2.3 to about 150 cst at 100° C. Preferably, the fluids have a viscosity index (VI) from about −100 to about 300, more preferably from about 0 to 280, and even more preferably from about 50 to 250. As used herein, viscosity ($Kv_{100}$) is determined by ASTM D 445-01, and viscosity index (VI) is determined by ASTM D 2270-93 (1998).

The fluids of this disclosure have a Noack volatility of no greater than 90 percent, preferably no greater than 80 percent, and more preferably no greater than about 50 percent. As used herein, Noack volatility is determined by ASTM D-5800. In particular, the fluids of this disclosure can function in engines without volatilization at specific temperatures (e.g., 247-249° C., Noack conditions).

Illustrative $R_1$, $R_2$ and $R_5$ substituents include, for example, the residue of an aliphatic olefin, an aromatic olefin, a cycloaliphatic olefin, a vinyl ether, an acrylate, a methacrylate, a vinyl ester, a heteroatom-containing olefin, and the like, as described herein.

Illustrative $R_3$, $R_4$ and $R_6$ substituents include, for example, linear or branched alkyl groups having from 1 to about 20 carbon atoms, preferably linear or branched alkyl groups having from 1 to 10 carbon atoms, and more preferably linear or branched alkyl groups having from 1 to about 8 carbon atoms. Illustrative $R_3$, $R_4$ and $R_6$ substituents include, for example, methyl, ethyl, propyl, butyl, pentyl, hexyl, heptyl, octyl, and the like.

Illustrative compounds of formula (1) and formula (2) are described herein.

Methods for the production of the alkylated siloxane-containing and alkylated alkoxy silane-containing cobasestock components suitable for use in the present disclosure are described herein.

The alkylated siloxane-containing and alkylated alkoxy silane-containing cobasestock component is preferably present in an amount sufficient for providing solubility and dispersancy of polar additives and/or sludge in the lubricating oil. The alkylated siloxane-containing and alkylated alkoxy silane-containing cobasestock component is present in the lubricating oils of this disclosure in an amount from 1 to about 99 weight percent, preferably from about 5 to about 95 weight percent, and more preferably from 10 to about 90 weight percent.

Other Additives

The formulated lubricating oil useful in the present disclosure may additionally contain one or more of the other commonly used lubricating oil performance additives including but not limited to dispersants, other detergents, corrosion inhibitors, rust inhibitors, metal deactivators, other anti-wear agents and/or extreme pressure additives, anti-seizure agents, wax modifiers, viscosity index improvers, viscosity modifiers, fluid-loss additives, seal compatibility agents, other friction modifiers, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives Chemistry and Applications" edited by Leslie R. Rudnick, Marcel Dekker, Inc. New York, 2003 ISBN: 0-8247-0857-1.

The types and quantities of performance additives used in combination with the instant disclosure in lubricant compositions are not limited by the examples shown herein as illustrations.

Viscosity Improvers

Viscosity improvers (also known as Viscosity Index modifiers, and VI improvers) increase the viscosity of the oil composition at elevated temperatures which increases film thickness, while having limited effect on viscosity at low temperatures.

Suitable viscosity improvers include high molecular weight hydrocarbons, polyesters and viscosity index improver dispersants that function as both a viscosity index improver and a dispersant. Typical molecular weights of these polymers are between 10,000 to 1,000,000, more typically about 20,000 to 500,000, and even more typically between about 50,000 and 200,000.

Examples of suitable viscosity improvers are polymers and copolymers of methacrylate, butadiene, olefins, or alkylated styrenes. Polyisobutylene is a commonly used viscosity index improver. Another suitable viscosity index improver is polymethacrylate (copolymers of various chain length alkyl methacrylates, for example), some formulations of which also serve as pour point depressants. Other suitable viscosity index improvers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The amount of viscosity modifier may range from zero to 8 wt %, preferably zero to 4 wt %, more preferably zero to 2 wt % based on active ingredient and depending on the specific viscosity modifier used.

Antioxidants

Typical antioxidant include phenolic antioxidants, aminic antioxidants and oil-soluble copper complexes.

The phenolic antioxidants include sulfurized and non-sulfurized phenolic antioxidants. The terms "phenolic type" or "phenolic antioxidant" used herein includes compounds having one or more than one hydroxyl group bound to an aromatic ring which may itself be mononuclear, e.g., benzyl, or poly-nuclear, e.g., naphthyl and spiro aromatic compounds. Thus "phenol type" includes phenol per se, catechol, resorcinol, hydroquinone, naphthol, etc., as well as alkyl or alkenyl and sulfurized alkyl or alkenyl derivatives thereof, and bisphenol type compounds including such bi-phenol compounds linked by alkylene bridges sulfuric bridges or oxygen bridges. Alkyl phenols include mono- and poly-alkyl or alkenyl phenols, the alkyl or alkenyl group containing from about 3-100 carbons, preferably 4 to 50 carbons and sulfurized derivatives thereof, the number of alkyl or alkenyl groups present in the aromatic ring ranging from 1 to up to the available unsatisfied valences of the aromatic ring remaining after counting the number of hydroxyl groups bound to the aromatic ring.

Generally, therefore, the phenolic anti-oxidant may be represented by the general formula:

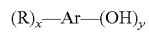

where Ar is selected from the group consisting of:

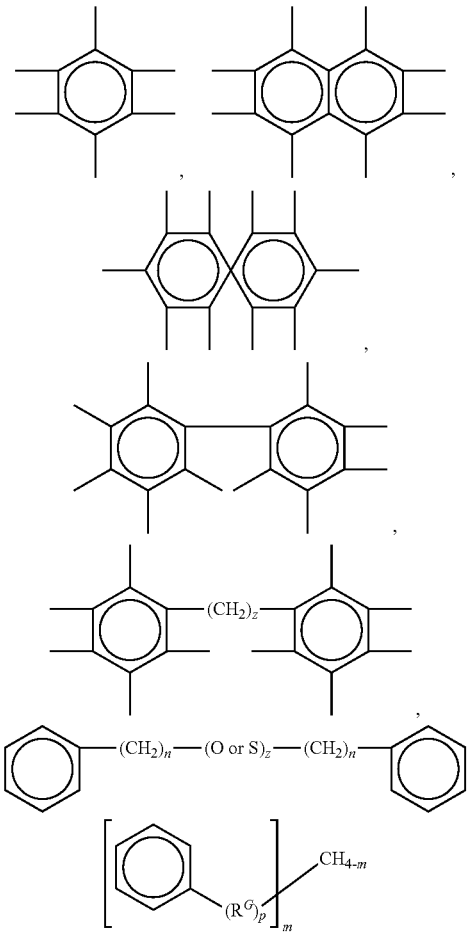

wherein R is a $C_3$-$C_{100}$ alkyl or alkenyl group, a sulfur substituted alkyl or alkenyl group, preferably a $C_4$-$C_{50}$ alkyl or alkenyl group or sulfur substituted alkyl or alkenyl group, more preferably $C_3$-$C_{100}$ alkyl or sulfur substituted alkyl group, most preferably a $C_4$-$C_{50}$ alkyl group, $R^G$ is a $C_1$-$C_{100}$ alkylene or sulfur substituted alkylene group, preferably a $C_2$-$C_{50}$ alkylene or sulfur substituted alkylene group, more preferably a $C_2$-$C_2$ alkylene or sulfur substituted alkylene group, y is at least 1 to up to the available valences of Ar, x ranges from 0 to up to the available valances of Ar-y, z ranges from 1 to 10, n ranges from 0 to 20, and m is 0 to 4 and p is 0 or 1, preferably y ranges from 1 to 3, x ranges from 0 to 3, z ranges from 1 to 4 and n ranges from 0 to 5, and p is 0.

Preferred phenolic antioxidant compounds are the hindered phenolics and phenolic esters which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_1$+ alkyl groups and the alkylene coupled derivatives of these hindered phenols. Examples of phenolic materials of this type 2-t-butyl-4-heptyl phenol; 2-t-butyl-4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; 2-methyl-6-t-butyl-4-dodecyl phenol; 2,6-di-t-butyl-4 methyl phenol; 2,6-di-t-butyl-4-ethyl phenol; and 2,6-di-t-butyl 4 alkoxy phenol; and

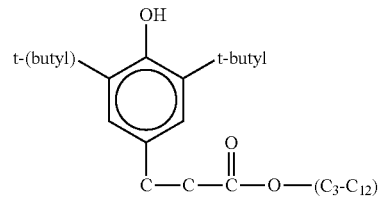

Phenolic type antioxidants are well known in the lubricating industry and commercial examples such as Ethanox® 4710, Irganox® 1076, Irganox® L1035, Irganox® 1010, Irganox® L109, Irganox® L118, Irganox® L135 and the like are familiar to those skilled in the art. The above is presented only by way of exemplification, not limitation on the type of phenolic antioxidants which can be used.

The phenolic antioxidant can be employed in an amount in the range of about 0.1 to 3 wt %, preferably 1 to 3 wt %, more preferably 1.5 to 3 wt % on an active ingredient basis.

Aromatic amine antioxidants include phenyl-α-naphthyl amine which is described by the following molecular structure:

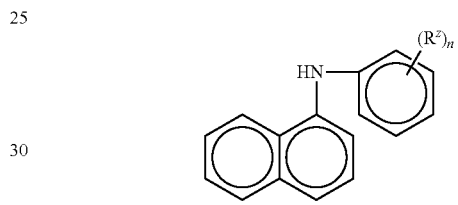

wherein $R^z$ is hydrogen or a $C_1$ to $C_{14}$ linear or $C_3$ to $C_{14}$ branched alkyl group, preferably $C_1$ to $C_{10}$ linear or $C_3$ to $C_{10}$ branched alkyl group, more preferably linear or branched $C_6$ to $C_8$ and n is an integer ranging from 1 to 5 preferably 1. A particular example is Irganox L06.

Other aromatic amine anti-oxidants include other alkylated and non-alkylated aromatic amines such as aromatic monoamines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least about 6 carbon atoms. Examples of aliphatic groups include hexyl, heptyl, octyl, nonyl, and decyl. Generally, the aliphatic groups will not contain more than 14 carbon atoms. The general types of such other additional amine antioxidants which may be present include diphenylamines, phenothiazines, imidodibenzyls and diphenyl phenylene diamines. Mixtures of two or more of such other additional aromatic amines may also be present. Polymeric amine antioxidants can also be used.

Another class of antioxidant used in lubricating oil compositions and which may also be present are oil-soluble copper compounds. Any oil-soluble suitable copper compound may be blended into the lubricating oil. Examples of suitable copper antioxidants include copper dihydrocarbyl thio- or dithiophosphates and copper salts of carboxylic acid (naturally occurring or synthetic). Other suitable copper salts include copper dithiacarbamates, sulphonates, phenates, and acetylacetonates. Basic, neutral, or acidic copper Cu(I) and or Cu(II) salts derived from alkenyl succinic acids or anhydrides are known to be particularly useful.

Such antioxidants may be used individually or as mixtures of one or more types of antioxidants, the total amount employed being an amount of about 0.50 to 5 wt %, preferably about 0.75 to 3 wt % (on an as-received basis).

Detergents

In addition to the alkali or alkaline earth metal salicylate detergent which is an essential component in the present disclosure, other detergents may also be present. While such other detergents can be present, it is preferred that the amount employed be such as to not interfere with the synergistic effect attributable to the presence of the salicylate. Therefore, most preferably such other detergents are not employed.

If such additional detergents are present, they can include alkali and alkaline earth metal phenates, sulfonates, carboxylates, phosphonates and mixtures thereof. These supplemental detergents can have total base number (TBN) ranging from neutral to highly overbased, i.e. TBN of 0 to over 500, preferably 2 to 400, more preferably 5 to 300, and they can be present either individually or in combination with each other in an amount in the range of from 0 to 10 wt %, preferably 0.5 to 5 wt % (active ingredient) based on the total weight of the formulated lubricating oil. As previously stated, however, it is preferred that such other detergent not be present in the formulation.

Such additional other detergents include by way of example and not limitation calcium phenates, calcium sulfonates, magnesium phenates, magnesium sulfonates and other related components (including borated detergents).

Dispersants

During engine operation, oil-insoluble oxidation byproducts are produced. Dispersants help keep these byproducts in solution, thus diminishing their deposition on metal surfaces. Dispersants may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the alkenylsuccinic derivatives, typically produced by the reaction of a long chain substituted alkenyl succinic compound, usually a substituted succinic anhydride, with a polyhydroxy or polyamino compound. The long chain group constituting the oleophilic portion of the molecule which confers solubility in the oil, is normally a polyisobutylene group. Many examples of this type of dispersant are well known commercially and in the literature. Exemplary patents describing such dispersants are U.S. Pat. Nos. 3,172,892; 3,219,666; 3,316,177 and 4,234,435. Other types of dispersants are described in U.S. Pat. Nos. 3,036,003; and 5,705,458.

Hydrocarbyl-substituted succinic acid compounds are popular dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between alkenyl succinic anhydrides and amines. Molar ratios can vary depending on the amine or polyamine. For example, the molar ratio of alkenyl succinic anhydride to TEPA can vary from 1:1 to about 5:1.

Succinate esters are formed by the condensation reaction between alkenyl succinic anhydrides and alcohols or polyols. Molar ratios can vary depending on the alcohol or polyol used. For example, the condensation product of an alkenyl succinic anhydride and pentaerythritol is a useful dispersant.

Succinate ester amides are formed by condensation reaction between alkenyl succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine.

The molecular weight of the alkenyl succinic anhydrides will typically range between 800 and 2,500. The above products can be post-reacted with various reagents such as sulfur, oxygen, formaldehyde, carboxylic acids such as oleic acid, and boron compounds such as borate esters or highly borated dispersants. The dispersants can be borated with from about 0.1 to about 5 moles of boron per mole of dispersant reaction product.

Mannich base dispersants are made from the reaction of alkylphenols, formaldehyde, and amines. Process aids and catalysts, such as oleic acid and sulfonic acids, can also be part of the reaction mixture. Molecular weights of the alkylphenols range from 800 to 2,500.

Typical high molecular weight aliphatic acid modified Mannich condensation products can be prepared from high molecular weight alkyl-substituted hydroxyaromatics or $HN(R)_2$ group-containing reactants.

Examples of high molecular weight alkyl-substituted hydroxyaromatic compounds are polypropylphenol, polybutylphenol, and other polyalkylphenols. These polyalkylphenols can be obtained by the alkylation, in the presence of an alkylating catalyst, such as $BF_3$, of phenol with high molecular weight polypropylene, polybutylene, and other polyalkylene compounds to give alkyl substituents on the benzene ring of phenol having an average 600-100,000 molecular weight.

Examples of $HN(R)_2$ group-containing reactants are alkylene polyamines, principally polyethylene polyamines. Other representative organic compounds containing at least one $HN(R)_2$ group suitable for use in the preparation of Mannich condensation products are well known and include the mono- and diamino alkanes and their substituted analogs, e.g., ethylamine and diethanol amine; aromatic diamines, e.g., phenylene diamine, diamino naphthalenes; heterocyclic amines, e.g., morpholine, pyrrole, pyrrolidine, imidazole, imidazolidine, and piperidine; melamine and their substituted analogs.

Examples of alkylene polyamine reactants include ethylenediamine, diethylene triamine, triethylene tetraamine, tetraethylene pentaamine, pentaethylene hexamine, hexaethylene heptaamine, heptaethylene octaamine, octaethylene nonaamine, nonaethylene decamine, and decaethylene undecamine and mixture of such amines having nitrogen contents corresponding to the alkylene polyamines, in the formula $H_2N$—$(Z$—$NH$—$)_nH$, mentioned before, Z is a divalent ethylene and n is 1 to 10 of the foregoing formula. Corresponding propylene polyamines such as propylene diamine and di-, tri-, tetra-, pentapropylene tri-, tetra-, penta- and hexaamines are also suitable reactants. The alkylene polyamines are usually obtained by the reaction of ammonia and dihalo alkanes, such as dichloro alkanes. Thus the alkylene polyamines obtained from the reaction of 2 to 11 moles of ammonia with 1 to 10 moles of dichloroalkanes having 2 to 6 carbon atoms and the chlorines on different carbons are suitable alkylene polyamine reactants.

Aldehyde reactants useful in the preparation of the high molecular products useful in this disclosure include the aliphatic aldehydes such as formaldehyde (also as paraformaldehyde and formalin), acetaldehyde and aldol (β-hydroxybutyraldehyde). Formaldehyde or a formaldehyde-yielding reactant is preferred.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000 or a mixture of such hydrocarbylene groups. Other preferred dispersants include succinic acid-esters and amides, alkylphenol-polyamine-coupled Mannich adducts, their capped derivatives, and other related components. Such additives may be used in an amount of about 0.1 to 20 wt %, preferably about 0.1 to 8 wt %, more preferably 1 to 6 wt % (on an as-received basis) based on the weight of the total lubricant.

Pour Point Depressants

Conventional pour point depressants (also known as lube oil flow improvers) may also be present. Pour point depressant may be added to lower the minimum temperature at which the fluid will flow or can be poured. Examples of suitable pour point depressants include alkylated naphthalenes polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. Such additives may be used in amount of about 0.0 to 0.5 wt %, preferably about 0 to 0.3 wt %, more preferably about 0.001 to 0.1 wt % on an as-received basis.

Corrosion Inhibitors/Metal Deactivators

Corrosion inhibitors are used to reduce the degradation of metallic parts that are in contact with the lubricating oil composition. Suitable corrosion inhibitors include aryl thiazines, alkyl substituted dimercapto thiodiazoles thiadiazoles and mixtures thereof. Such additives may be used in an amount of about 0.01 to 5 wt %, preferably about 0.01 to 1.5 wt %, more preferably about 0.01 to 0.2 wt %, still more preferably about 0.01 to 0.1 wt % (on an as-received basis) based on the total weight of the lubricating oil composition.

Seal Compatibility Additives

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride and sulfolane-type seal swell agents such as Lubrizol 730-type seal swell additives. Such additives may be used in an amount of about 0.01 to 3 wt %, preferably about 0.01 to 2 wt % on an as-received basis.

Anti-Foam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 percent, preferably 0.001 to about 0.5 wt %, more preferably about 0.001 to about 0.2 wt %, still more preferably about 0.0001 to 0.15 wt % (on an as-received basis) based on the total weight of the lubricating oil composition.

Inhibitors and Antirust Additives

Antirust additives (or corrosion inhibitors) are additives that protect lubricated metal surfaces against chemical attack by water or other contaminants. One type of anti-rust additive is a polar compound that wets the metal surface preferentially, protecting it with a film of oil. Another type of anti-rust additive absorbs water by incorporating it in a water-in-oil emulsion so that only the oil touches the surface. Yet another type of anti-rust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 wt %, preferably about 0.01 to 1.5 wt % on an as-received basis.

In addition to the ZDDP antiwear additives which are essential components of the present disclosure, other antiwear additives can be present, including zinc dithiocarbamates, molybdenum dialkyldithiophosphates, molybdenum dithiocarbamates, other organo molybdenum-nitrogen complexes, sulfurized olefins, etc.

The term "organo molybdenum-nitrogen complexes" embraces the organo molybdenum-nitrogen complexes described in U.S. Pat. No. 4,889,647. The complexes are reaction products of a fatty oil, dithanolamine and a molybdenum source. Specific chemical structures have not been assigned to the complexes. U.S. Pat. No. 4,889,647 reports an infrared spectrum for a typical reaction product of that disclosure; the spectrum identifies an ester carbonyl band at 1740 cm$^{-1}$ and an amide carbonyl band at 1620 cm$^{-1}$. The fatty oils are glyceryl esters of higher fatty acids containing at least 12 carbon atoms up to 22 carbon atoms or more. The molybdenum source is an oxygen-containing compound such as ammonium molybdates, molybdenum oxides and mixtures.

Other organo molybdenum complexes which can be used in the present disclosure are tri-nuclear molybdenum-sulfur compounds described in EP 1 040 115 and WO 99/31113 and the molybdenum complexes described in U.S. Pat. No. 4,978,464.

In the above detailed description, the specific embodiments of this disclosure have been described in connection with its preferred embodiments. However, to the extent that the above description is specific to a particular embodiment or a particular use of this disclosure, this is intended to be illustrative only and merely provides a concise description of the exemplary embodiments. Accordingly, the disclosure is not limited to the specific embodiments described above, but rather, the disclosure includes all alternatives, modifications, and equivalents falling within the true scope of the appended claims. Various modifications and variations of this disclosure will be obvious to a worker skilled in the art and it is to be understood that such modifications and variations are to be included within the purview of this application and the spirit and scope of the claims.

EXAMPLES

Example 1

Synthesis of 1,3-didecyl-1,1,3,3-tetramethyl disiloxane

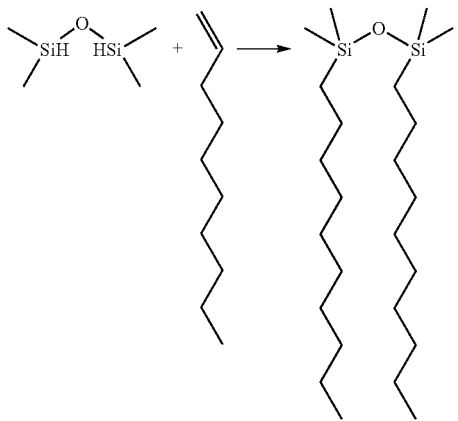

1-Decene (13.1 grams, 0.0931 mol), 1,1,3,3-tetramethyl-disiloxane (2.50 grams, 0.00186 mol) and 10 milligrams PtO$_2$ were charged in a 25 milliliter thick glass reactor. The reaction mixture was heated at 80° C. for 12 hours. The mixture was cooled to room temperature, saturated with air by bubbling air through the mixture for 30 seconds and then the mixture was heated to a temperature 85° C. for 2 hours. After cooling down to room temperature the PtO$_2$ catalyst removed by filtration and excess of unreacted 1-decene by a rotary evaporator and high boiling components with vacuum oven at 180° C. with high vacuum for 1 hour. The final product yield was 7.7 grams (yield 90%). The product IR and $^1$H NMR analysis (FIG. 1) suggests the formation of alkyl disiloxane. IR: neat (cm$^{-1}$): 2921, 2850, 2305, 2165, 1715, 1519, 1377, 1303, 720. $^1$H NMR (CDCl$_3$): δ 1.24 (m, 32H, —CH$_2$—), 0.86 (t, 6H, —CH$_3$), 0.47 (t, 4H, —SiCH$_2$—), 0.00 (s, 12H, Si—CH$_3$). FIG. 1 shows the $^1$HNMR spectra of 1,3-didecyl-1,1,3,3-tetrameyhyl disiloxane (bottom spectrum, 26232-71) and 1-decene starting olefin.

Example 2

Synthesis of 1,3-didodecyl-1,1,3,3-tetramethyl disiloxane

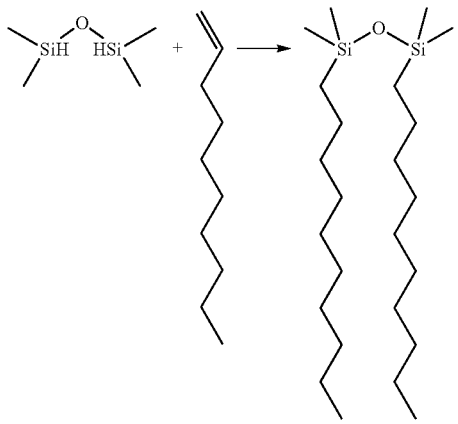

Figure 2:
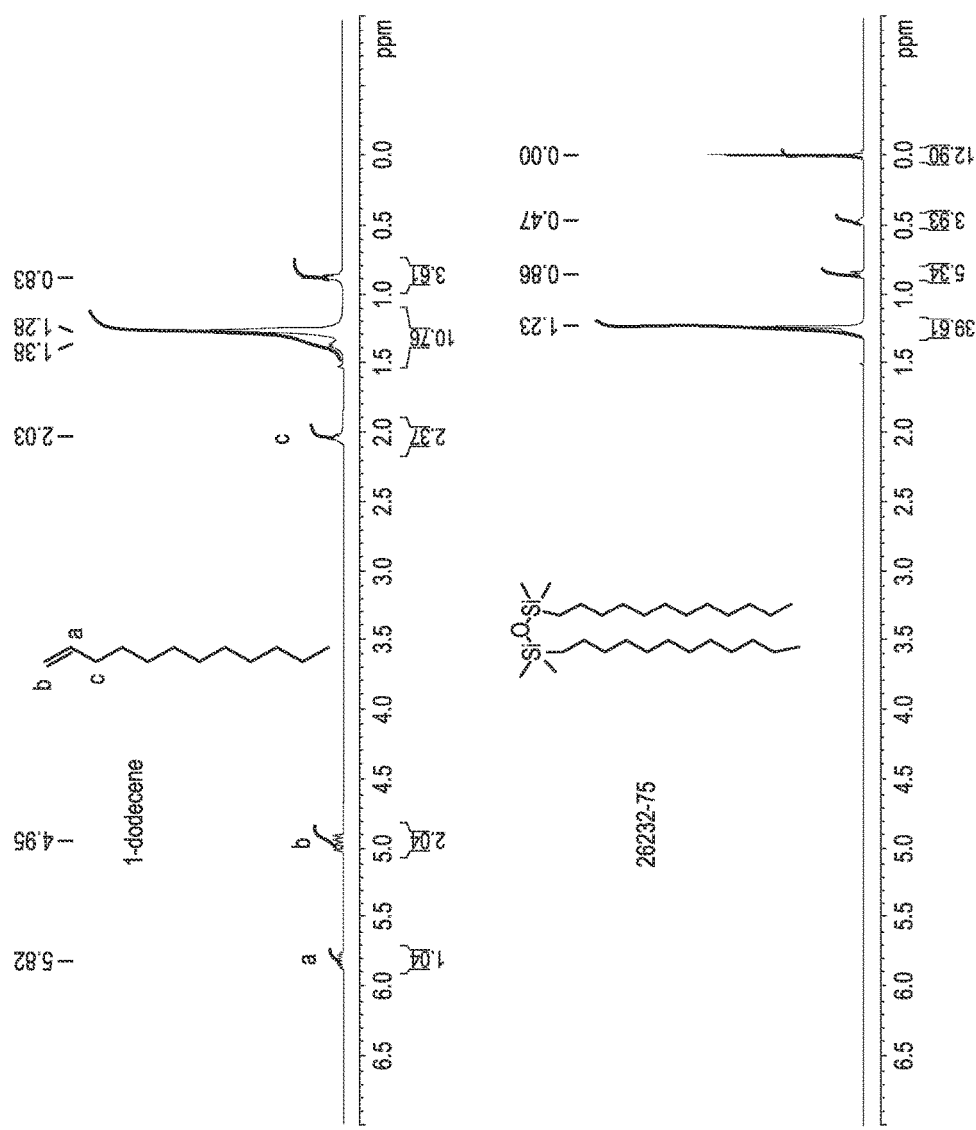
FIG. 2 shows $^1$H NMR spectra for 1-dodecene starting olefin (top spectrum) and 1,3-didodecyl-1,1,3,3-tetramethyl disiloxane (bottom spectrum) for Example 2.

1-Dodecene (15.6 grams, 0.0931 mol), 1,1,3,3-tetramethyldisiloxane (2.50 grams, 0.00186 mol) and 10 milligrams PtO$_2$ were charged in a 25 milliliter thick glass reactor. The reaction mixture was heated at 80° C. for 12 hours. The mixture was cooled to room temperature, saturated with air by bubbling air through the mixture for 30 seconds and then the mixture was heated at a temperature of 85° C. for 18 hours. After cooling down to room temperature the PtO$_2$ catalyst was removed by filtration and excess of unreacted 1-dodecene by a rotary evaporator and high boiling components with vacuum oven at 180° C. with high vacuum for 1 hour. The final product was yielded 8.5 grams (yield 97%). The product IR and $^1$H NMR analysis (FIG. 2) suggests the formation of alkyl disiloxane. IR: neat (cm$^{-1}$): 2956, 2923, 2853, 1467, 1409, 1378, 1252, 1060, 840, 795, 721, 704. $^1$H NMR (CDCl$_3$): δ 1.23 (m, 40H, —CH$_2$—), 0.86 (t, 6H, —CH$_3$), 0.47 (t, 4H, —SiCH$_2$—), 0.00 (s, 12H, Si—CH$_3$). FIG. 2 shows the $^1$HNMR spectra of 1,3-didodecyl-1,1,3,3-tetrameyhyl disiloxane (bottom spectrum, 26232-75) and 1-dodecene starting olefin.

Example 3

Synthesis of 1,3-di(2-hexyldecyl)-1,1,3,3-tetramethyl disiloxane

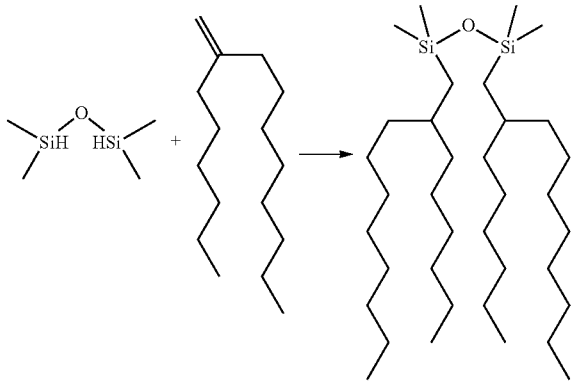

Figure 3:
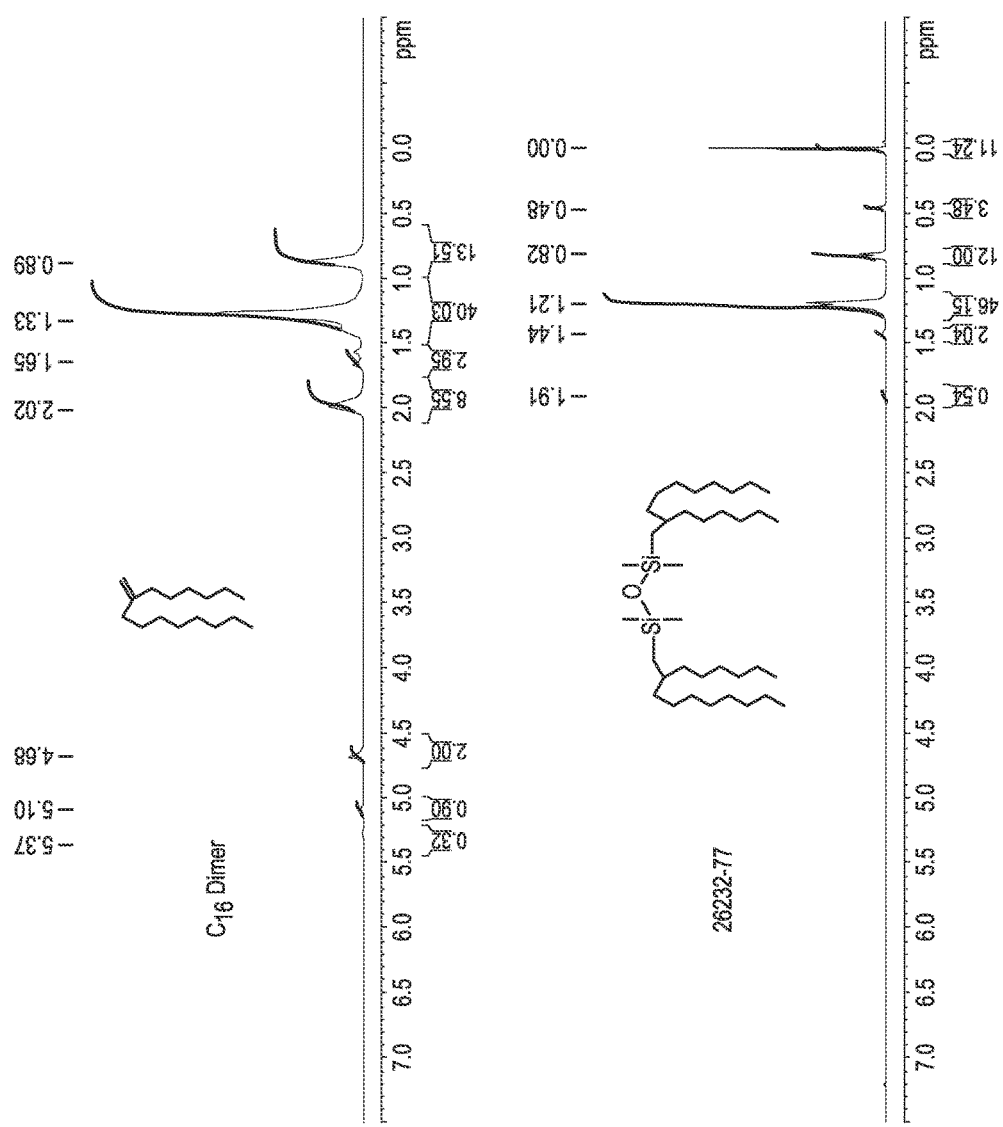
FIG. 3 shows $^1$H NMR spectra for C$_{16}$-dimer starting olefin (top spectrum) and 1,3-di(2-hexyldecyl)-1,1,3,3-tetramethyl disiloxane (bottom spectrum) for Example 3.

C$_{16}$ dimer (16.6 grams, 0.0744 mol), 1,1,3,3-tetramethyl-disiloxane (2.50 grams, 0.00186 mol) and 20 milligrams PtO$_2$ were charged in a 25 milliliter thick glass reactor. The reaction mixture was heated at 115° C. for 12 hours. The mixture was cooled to room temperature, saturated with air by bubbling air through the mixture for 30 seconds and then the mixture was heated at a temperature of 115° C. for 18 hours. After cooling down to room temperature, the PtO$_2$ catalyst was removed by filtration and excess of unreacted C$_{16}$ dimer with vacuum oven at 200° C. with high vacuum for 1.5 hours. The final product yielded 9.0 grams (97%). The product IR and $^1$H NMR analysis (FIG. 3) suggests the formation of alkyl disiloxane. IR: neat (cm$^{-1}$): 2956, 2854, 2923, 1467, 1378, 1252, 1054, 839, 804, 722. $^1$H NMR (CDCl$_3$): δ 1.22 (m, 48H, —CH$_2$—), 0.86 (t, 12H, —CH$_3$), 0.47 (d, 4H, —SiCH$_2$—), 0.00 (s, 12H, Si—CH$_3$). FIG. 3 shows the $^1$HNMR spectra of 1,3-di(2-hexyldecyl)-1,1,3,3-tetrameyhyl disiloxane (bottom spectrum, 26232-77) and C$_{16}$-dimer olefin.

Example 4

Synthesis of Trimethoxy (Octadecyl) Silane

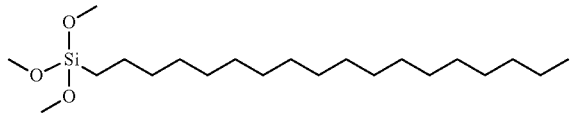 [SMILES: CCCCCCCCCCCCCCCCCC[Si](OC)(OC)OC]

The hydrosilylation reaction of 1-octadecene and trimethoxysilane is carried out using hexachloro-platinic acid catalyst in 2-propyl alcohol, $H_2[PtCl_6] \cdot 6H_2O$. The mole ratio of 1.5 mole equivalent 1-octadecene, 1.0 mole equivalent trimethoxysilane and $5 \times 10^{-5}$ mole equivalent $H_2[PtCl_6] \cdot 6H_2O$ in 2-propanol is initiated at 100-120° C. temperatures under moisture and oxygen free inert conditions. After the reaction, the reaction mixture is cooled down to room temperature and the catalyst is removed by filtration. The excess of unreacted 1-ocatadecene is removed by distillation under vacuum. The final product is qualitatively yielded. The NMR and FT-IR show the formation of trimethoxy (octadecyl) silane.

Example 5

Lubricant Properties of Basestocks

The kinematic viscosity (Kv) of the liquid products was measured using ASTM standards D-445 and reported at temperatures of 100° C. (Kv at 100° C.) or 40° C. (Kv at 40° C.). The viscosity index (VI) was measured according to ASTM standard D-2270 using the measured kinematic viscosities for each product. The product volatility was measured using thermogravimetric analysis (TGA Noack). The lube properties were evaluated and the data are reported in Table 1 below.

Figure 4:
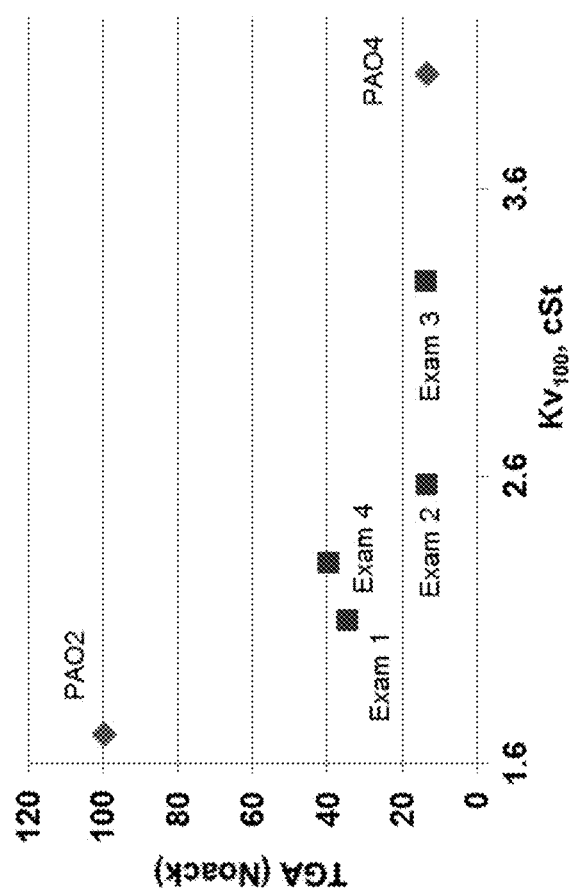
FIG. 4 graphically shows kinematic viscosity (Kv$_{100}$) cst at 100° C. (x axis) and TGA (Noack) (y axis) of PAO2, PAO4 and the synthetic fluids of Examples 1-4.

The fluids listed in Table 1 were evaluated as synthetic basestocks and found to have good lubricant properties. These fluids can be used as lubricant basestocks and co-basestocks. These fluids have low viscosities, lower volatility and very high viscosity index. For example, the fluid of the Example 2 with $KV_{100}$ of 2.57 cSt has exceptionally high VI of 211, while TGA volatility is comparable to PAO4. All these synthetic basestocks have excellent viscosity index. The relative volatility of the basestocks along with PAO2 and PAO4 were measured using TGA Noack test. The TGA Noack data of the fluids of Examples 1-4 show that they have relatively low volatility compared to hydrocarbon fluids like PAO2 and PAO4. FIG. 4 shows the kinematic viscosity at 100° C. (x-axis) and TGA (Noack) (y-axis) of PAO2, PAO4 and synthetic fluids of Examples 1-4.

TABLE 1

| Basestock # | $Kv_{100}$ ° C. | $Kv_{40}$ ° C. | VI | TGA Noack |
|---|---|---|---|---|
| Example 1 | 2.10 | 5.75 | 205 | 34.62 |
| Example 2 | 2.57 | 8.66 | 211 | 13.52 |
| Example 3 | 3.28 | 12.10 | 147 | 13.62 |
| Example 4 | 2.30 | 6.70 | 184 | 39.63 |
| PAO2 | 1.7 | 5 | — | 99.73 |
| PAO4 | 4.10 | 19.00 | 126 | 13.45 |

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A composition comprising one or more compounds represented by the formula:

$$R_1\text{—Si}(R_3)_2\text{—O—Si}(R_4)_2\text{—}R_2 \quad (1)$$

wherein $R_1$ and $R_2$ are the same or different and are the saturated residue of an olefin having from about 4 to about 40 carbon atoms; and each $R_3$ and $R_4$ are the same or different and are an alkyl group having from 1 to about 20 carbon atoms;

wherein the olefin is selected from the group consisting of an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300.

2. The composition of claim 1 wherein:

the aromatic olefin is selected from 2,4-dimethylstyrene, 2,5-dimethylstyrene, 4-tert-butyl styrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl] styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene.

3. The composition of claim 1 wherein:

the cycloaliphatic olefin is selected from vinylcyclopentane, vinylcylcohexane, cyclopentene, cyclohexene, cycloheptene, cyclooctene, cyclononene, cyclodecene, cylododecene, cyclotetradecene, cyclohexadecene, cyclooctadecene, allylcyclohexane, 1,2,4-trivinylcyclohexane, and 5-vinyl-2-norbornene.

4. The composition of claim 1 wherein:
the vinyl ether is selected from ethyl vinyl ether, propyl vinyl ether, butyl vinyl ether, isobutyl vinyl ether, 2-ethylhexyl vinyl ether, dodecyl vinyl ether, tetraethylene glycol methyl vinyl ether, hexadecyl vinyl ether, octadecyl vinyl ether, isooctyl vinyl ether, t-butyl vinyl ether, phenyl vinyl ether, cyclohexyl vinyl ether, 2,2,2-trifluoroethyl vinyl ether, 1,4-butanediol divinyl ether, di(ethylene glycol) divinyl ether, tri(ethylene glycol) divinyl ether, 1,4-cyclohexanedimethanol divinyl ether, bis[4-(vinyloxy)butyl] isophthalate, bis[4-(vinyloxy)butyl] succinate, diethyl vinyl orthoformate, di(ethylene glycol) vinyl ether, ethylene glycol vinyl ether, and 1,4-butanediol vinyl ether.

5. The composition of claim 1 wherein:
the acrylate is selected from methyl acrylate, ethyl acrylate, hexyl acrylate, isooctyl acrylate, isodecyl acrylate, lauryl acrylate, octadecyl acrylate, di(ethylene glycol) 2-ethylhexyl ether acrylate, di(ethylene glycol) ethyl ether acrylate, ethylene glycol phenyl ether acrylate, 2-ethylhexyl acrylate, butyl acrylate, isobornyl acrylate, ethylene glycol methyl ether acrylate, 2-(dimethylamino)ethyl acrylate, 2-(diethylamino)ethyl acrylate, 3-(dimethylamino)propyl acrylate, pentafluorophenyl acrylate, 1,6-hexanediol diacrylate, trimethylolpropane triacrylate, 4-acetoxyphenethyl acrylate, 4-allyloxy-2-hydroxybenzophenone, 2-(4-benzoyl-3-hydroxyphenoxy)ethyl acrylate, 4-acryloylmorpholine, 4-tert-butylcyclohexyl acrylate, tetrahydrofurfutyl acrylate, 3,5,5-trimethylhexyl acrylate, di(trimethylolpropane) tetraacrylate, tris[2-(acryloyloxy)ethyl]isocyanurate, pentaerythritol tetraacrylate, 1,3,5-triallyl-1,3,5-triazine-2,4,6(1H,3H,5H)-trione, 1,3,5-triacryloylhexahydro-1,3,5-triazine, 1,1,1,3,3,3-hexafluoroisopropyl acrylate, 9H-carbazole-9-ethyl acrylate, and 2-hydroxypropyl 2-(methacryloyloxy)ethyl phthalate.

6. The composition of claim 1 wherein:
the methacrylate is selected from methyl methacrylate, butyl methacrylate, tert-butyl methacrylate, hexyl methacrylate, 2-ethylhexyl methacrylate, 2-(dimethylamino)ethyl methacrylate, 2-(diethylamino)ethyl methacrylate, di(ethylene glycol) methyl ether methacrylate, lauryl methacrylate, stearyl methacrylate, isobornyl methacrylate, ethylene glycol phenyl ether methacrylate, phenyl methacrylate, cyclohexyl methacrylate, allyl methacrylate, vinyl methacrylate, benzyl methacrylate, 1,6-hexanediol dimethacrylate, bisphenol A dimethacrylate, bisphenol A glycerolate dimethacrylate, 2-[3-(2H-benzotriazol-2-yl)-4-hydroxyphenyl] ethyl methacrylate, cyclohexyl methacrylate, tetrahydrofurfutyl methacrylate, 2-(tert-butylamino)ethyl methacrylate, 2-(diisopropylamino)ethyl methacrylate, 2-N-morpholinoethyl methacrylate, 9H-carbazole-9-ethyl methacrylate, 1-naphthyl methacrylate, pentafluorophenyl methacrylate, 1-pyrenemethayl methacrylate, TEMPO methacrylate, and N-(triphenylmethyl) methacrylamide.

7. The composition of claim 1 wherein:
the vinyl ester is selected from vinyl acetate, vinyl propionate, vinyl valerate, vinyl butyrate, vinyl decanoate, vinyl stearate, vinyl cinnamate, allyl butyrate, vinyl pivalate, vinyl benzoate, vinyl 4-t-butylbenzoate, and allyl cinnamate.

8. The composition of claim 1 wherein:
the heteroatom-containing olefin is selected from N-methyl-N-vinylacetamide, N,N-dimethylacrylamide, 4-vinylpyridine, 2-vinylpyridine, 1-vinyl-2-pyrrolidinone, 1-vinyl-1,2,4-triazole, 1-vinylimidazole, N-vinylcaprolactone, 4-acryloylmorpholine, 5-vinyluracil, 4-acryloylmorpholine, N,N-dimethylacrylamide, 2-vinyl-1,3-dioxolane, acrolein diethyl acetal, acrolein dimethyl acetal, 4-vinyl-1,3-dioxolane-2-one, vinylbenzoic acid, 1-vinylbenzyl alcohol, vinyl trifluoroacetate, 1-vinyl cyclohexanole, vinyloxy trimethylsilane, vinyltrimethylsilane, allyl trimethylsilane, triphenyl(vinyl)silane, and 2-isopropenyl-2-oxazoline.

9. A process for preparing a composition comprising one or more compounds represented by the formula:

$$R_1-Si(R_3)_2-O-Si(R_4)_2-R_2 \qquad (1)$$

wherein $R_1$ and $R_2$ are the same or different and are the saturated residue of an olefin having from about 4 to about 40 carbon atoms; and each $R_3$ and $R_4$ are the same or different and are an alkyl group having from 1 to about 20 carbon atoms;

wherein said process comprises reacting an alkyl siloxane with an olefin, in the presence of a catalyst, under reaction conditions sufficient to produce said composition;

wherein the alkyl siloxane has from about 4 to about 20 carbon atoms; and the olefin is selected from the group consisting of an aromatic olefin, a cycloaliphatic olefin, a vinyl ether, an acrylate, a methacrylate, a vinyl ester, and a heteroatom-containing olefin; and wherein the composition has a viscosity ($Kv_{100}$) from about 2 to about 300 cst at 100° C., and a viscosity index (VI) from about −100 to about 300.

10. The process of claim 9 wherein the alkyl siloxane comprises 1,1,3,3-tetramethyldisiloxane, hexaethoxydisiloxane, 1,3-didecyl-1,1,3,3-tetramethyl disiloxane, 1,3-didodecyl-1,1,3,3-tetramethyl disiloxane, 3-di(2-hexyldecyl)-1,1,3,3-tetramethyl disiloxane, 1,3-bis(3-(2-hydroxyethyoxy)propyl)tetramethyldisiloxane, 1,3-bis(hydroxypropyl)tetramethyldisiloxane, bis(methoxytriethyleneoxypropyl)tetramethyldisiloxane, 1,3-bis(trimethylsilyoxy)1,3-dimethyldisiloxane, 1,3-bis(3-hydroxyisobutyl)tetramethyldisiloxane, or 1,3-diallyltetramethyldisiloxane.

11. The process of claim 9 wherein:
the aromatic olefin is selected from 2,4-dimethylstyrene, 2,5-dimethylstyrene, 4-tert-butyl styrene, 4-tert-butoxystyrene, 3,4-dimethoxystyrene, 4-acetoxystyrene, 1,3-diisopropenylbenzene, 4-ethoxystyrene, 2,3,4,5,6-pentafluorostyrene, 4-fluorostyrene, 1-(trifluoromethyl)-4-vinylbenzene, 4-[N-(methylaminoethyl)aminomethyl] styrene, 4-benzyloxy-3-methoxystyrene, 2-methoxy-4-vinylphenol, ((4-vinylphenyl)methylene)dibenzene, 1-vinylnaphthalene, 2-vinylnaphthalene, divinylbenzene, trivinylbenzene, styrene, 4-methyl styrene, 2-methyl styrene, 1-methyl styrene, 4-methoxystyrene, 2-methoxystyrene, 1-allyl-4-(trifluoromethyl)benzene, 9-vinylanthracene, 1,1-diphenylethylene, 2,3-dibenzyl-1,3-butadiene, 1-allyl-2-methylbenzene, dipentene, 4-vinylbiphenyl, 9-vinylcarbazole, N-vinylphthalimide, and 4-(trifluoromethyl)styrene.

12. The process of claim 9 wherein:
the cycloaliphatic olefin is selected from vinylcyclopentane, vinylcylcohexane, cyclopentene, cyclohexene, cycloheptene, cyclooctene, cyclononene, cyclodecene, cylododecene, cyclotetradecene, cyclohexadecene, cyclooctadecene, allylcyclohexane, 1,2,4-trivinylcyclohexane, and 5-vinyl-2-norbornene.

13. The process of claim 9 wherein:
the vinyl ether is selected from ethyl vinyl ether, propyl vinyl ether, butyl vinyl ether, isobutyl vinyl ether, 2-ethylhexyl vinyl ether, dodecyl vinyl ether, tetraethylene glycol methyl vinyl ether, hexadecyl vinyl ether, octadecyl vinyl ether, isooctyl vinyl ether, t-butyl vinyl ether, phenyl vinyl ether, cyclohexyl vinyl ether, 2,2,2-trifluoroethyl vinyl ether, 1,4-butanediol divinyl ether, di(ethylene glycol) divinyl ether, tri(ethylene glycol) divinyl ether, 1,4-cyclohexanedimethanol divinyl ether, bis[4-(vinyloxy)butyl] isophthalate, bis[4-(vinyloxy)butyl] succinate, diethyl vinyl orthoformate, di(ethylene glycol) vinyl ether, ethylene glycol vinyl ether, and 1,4-butanediol vinyl ether.

14. The process of claim 9 wherein:
the acrylate is selected from methyl acrylate, ethyl acrylate, hexyl acrylate, isooctyl acrylate, isodecyl acrylate, lauryl acrylate, octadecyl acrylate, di(ethylene glycol) 2-ethylhexyl ether acrylate, di(ethylene glycol) ethyl ether acrylate, ethylene glycol phenyl ether acrylate, 2-ethylhexyl acrylate, butyl acrylate, isobornyl acrylate, ethylene glycol methyl ether acrylate, 2-(dimethylamino)ethyl acrylate, 2-(diethylamino)ethyl acrylate, 3-(dimethylamino)propyl acrylate, pentafluorophenyl acrylate, 1,6-hexanediol diacrylate, trimethylolpropane triacrylate, 4-acetoxyphenethyl acrylate, 4-allyloxy-2-hydroxybenzophenone, 2-(4-benzoyl-3-hydroxyphenoxy)ethyl acrylate, 4-acryloylmorpholine, 4-tert-butylcyclohexyl acrylate, tetrahydrofurfutyl acrylate, 3,5,5-trimethylhexyl acrylate, di(trimethylolpropane) tetraacrylate, tris[2-(acryloyloxy)ethyl]isocyanurate, pentaerythritol tetraacrylate, 1,3,5-triallyl-1,3,5-triazine-2,4,6(1H,3H,5H)-trione, 1,3,5-triacryloylhexahydro-1,3,5-triazine, 1,1,1,3,3,3-hexafluoroisopropyl acrylate, 9H-carbazole-9-ethyl acrylate, and 2-hydroxypropyl 2-(methacryloyloxy)ethyl phthalate.

15. The process of claim 9 wherein:
the methacrylate is selected from methyl methacrylate, butyl methacrylate, tert-butyl methacrylate, hexyl methacrylate, 2-ethylhexyl methacrylate, 2-(dimethylamino)ethyl methacrylate, 2-(diethylamino)ethyl methacrylate, di(ethylene glycol) methyl ether methacrylate, lauryl methacrylate, stearyl methacrylate, isobornyl methacrylate, ethylene glycol phenyl ether methacrylate, phenyl methacrylate, cyclohexyl methacrylate, allyl methacrylate, vinyl methacrylate, benzyl methacrylate, 1,6-hexanediol dimethacrylate, bisphenol A dimethacrylate, bisphenol A glycerolate dimethacrylate, 2-[3-(2H-benzotriazol-2-yl)-4-hydroxyphenyl] ethyl methacrylate, cyclohexyl methacrylate, tetrahydrofurfutyl methacrylate, 2-(tert-butylamino)ethyl methacrylate, 2-(diisopropylamino)ethyl methacrylate, 2-N-morpholinoethyl methacrylate, 9H-carbazole-9-ethyl methacrylate, 1-naphthyl methacrylate, pentafluorophenyl methacrylate, 1-pyrenemethayl methacrylate, TEMPO methacrylate, and N-(triphenylmethyl) methacrylamide.

16. The process of claim 9 wherein:
the vinyl ester is selected from vinyl acetate, vinyl propionate, vinyl valerate, vinyl butyrate, vinyl decanoate, vinyl stearate, vinyl cinnamate, allyl butyrate, vinyl pivalate, vinyl benzoate, vinyl 4-t-butylbenzoate, and allyl cinnamate.

17. The process of claim 9 wherein:
the heteroatom-containing olefin is selected from N-methyl-N-vinylacetamide, N,N-dimethylacrylamide, 4-vinylpyridine, 2-vinylpyridine, 1-vinyl-2-pyrrolidinone, 1-vinyl-1,2,4-triazole, 1-vinylimidazole, N-vinylcaprolactone, 4-acryloylmorpholine, 5-vinyluracil, 4-acryloylmorpholine, N,N-dimethylacrylamide, 2-vinyl-1,3-dioxolane, acrolein diethyl acetal, acrolein dimethyl acetal, 4-vinyl-1,3-dioxolane-2-one, vinylbenzoic acid, 1-vinylbenzyl alcohol, vinyl trifluoroacetate, 1-vinyl cyclohexanole, vinyloxy trimethylsilane, vinyltrimethylsilane, allyl trimethylsilane, triphenyl(vinyl)silane, and 2-isopropenyl-2-oxazoline.

18. A method for improving one or more of solubility and dispersancy of polar additives or sludge in a lubricating oil by using as the lubricating oil a formulated oil comprising a lubricating oil basestock as a major component, and a lubricating oil cobasestock as a minor component; wherein said lubricating oil cobasestock comprises one or more compounds represented by the formula:

$$R_1\text{—Si}(R_3)_2\text{—O—Si}(R_4)_2\text{—}R_2 \quad (1)$$

wherein $R_1$ and $R_2$ are the same or different and are the saturated residue of an olefin having from about 4 to about 40 carbon atoms; and each $R_3$ and $R_4$ are the same or different and are an alkyl group having from 1 to about 20 carbon atoms;

wherein the olefin is selected from the group consisting of an aromatic olefin, a cycloaliphatic olefin, a vinyl ether, an acrylate, a methacrylate, a vinyl ester, and a heteroatom-containing olefin; and wherein the lubricating oil cobasestock has a viscosity ($Kv_{100}$) from about 2 to about 300 cst at 100° C., and a viscosity index (VI) from about −100 to about 300.

* * * * *